(12) United States Patent
Nagai et al.

(10) Patent No.: US 7,013,865 B2
(45) Date of Patent: Mar. 21, 2006

(54) FUEL INJECTION SYSTEM

(75) Inventors: Koichi Nagai, Toyoake (JP); Ryo Suenaga, Kariya (JP)

(73) Assignee: Denso Corporation, (JP)

( * ) Notice: Subject to any disclaimer, the term of this patent is extended or adjusted under 35 U.S.C. 154(b) by 0 days.

(21) Appl. No.: 11/118,324

(22) Filed: May 2, 2005

(65) Prior Publication Data

US 2005/0247285 A1     Nov. 10, 2005

(30) Foreign Application Priority Data

May 6, 2004    (JP)    ............................. 2004-137702

(51) Int. Cl.
*F02M 7/28*    (2006.01)
(52) U.S. Cl. .................. 123/305; 123/435; 701/105
(58) Field of Classification Search ........... 123/305, 123/435, 27 GE, 295, 299, 300, 526; 701/105
See application file for complete search history.

(56) References Cited

U.S. PATENT DOCUMENTS

| | | | | |
|---|---|---|---|---|
| 5,706,780 A | * | 1/1998 | Shirakawa | ............ 123/381 |
| 5,718,203 A | * | 2/1998 | Shimada et al. | ............ 123/305 |
| 6,722,345 B1 | * | 4/2004 | Saeki et al. | ............ 123/435 |

FOREIGN PATENT DOCUMENTS

| | | | |
|---|---|---|---|
| JP | 9-79068 | * | 3/1997 |
| JP | 9-158768 | * | 6/1997 |
| JP | 11-125141 | | 5/1999 |
| JP | 2000-291466 | | 10/2000 |
| WO | WO 2005/031139 | * | 4/2005 |

* cited by examiner

*Primary Examiner*—Hai Huynh
(74) *Attorney, Agent, or Firm*—Nixon & Vanderhye PC (57) ABSTRACT

A fuel injection system includes an injector, a controller, and a cylinder internal pressure sensor. The injector injects fuel to an engine. The controller controls injection start timing of the injector, an injection amount, and a supply pressure of the injected fuel. The cylinder internal pressure sensor detects one of a cylinder internal pressure and a heat release rate of the internal combustion engine. The controller has a standard estimator and a corrector. The standard state estimator obtains a standard state of one of the cylinder internal pressure and the heat release rate upon fuel injection from the injector. The corrector corrects at least one of the injection start timing, the injection amount, and the supply pressure in a direction to eliminate a difference that exists between the standard state obtained by the standard state estimator and one of the cylinder internal pressure and the heat release rate detected by the cylinder internal pressure sensor.

11 Claims, 3 Drawing Sheets

FUEL INJECTION SYSTEM

CROSS REFERENCE TO RELATED APPLICATIONS

This application is based upon and claims the benefit of priority of Japanese Patent Application No. 2004-137702, filed on May 6, 2004, the contents of which are incorporated herein by reference.

FIELD OF THE INVENTION

The present invention relates to a fuel injection system for an internal combustion engine and, more particularly, to a system for performing correction control of injection amount in accordance with fuel viscosity.

BACKGROUND OF THE INVENTION

A conventional controller of a fuel injection system calculates an optimum injection amount and an injection start timing and the like from various engine-related parameters. The, the fuel injection system supplies fuel to the engine by the injection amount obtained from the computation by drive-controlling the injector.

However, even if the accuracy of parts such as the injector is improved to the maximum, when the viscosity of the fuel supplied to the injector and/or fuel performance (e.g., a cetane value in the case of diesel engine, or an octane value in the case of gasoline engine) has been changed, the injection start timing, the injection amount, the combustion amount and the like change.

Then, an engine torque, obtained in correspondence with an accelerator opening changes. This causes degradation of drivability performance, causes difficulty in air-fuel ratio control with high accuracy, and further disturbs techniques for improving fuel cost to the maximum and improving exhaust gas performance to the maximum.

SUMMARY OF THE INVENTION

The present invention has been made in view of the above problem and the object of the invention is to provide a fuel injection system capable of correcting a combustion state to a standard state even when the viscosity or performance of fuel supplied to a vehicle has changed with respect to the standard state.

In one aspect of the fuel injection system according to the present invention, when there is a difference between the standard state obtained by a standard state estimation means and a cylinder internal pressure or a heat release rate detected by a cylinder internal pressure sensor upon fuel injection, a correction means corrects at least one of an injection start timing, an injection amount, and a supply pressure in a direction to eliminate the difference.

In this manner, the normal state is compared With the detected cylinder internal pressure or heat release rate, and when there is a difference between the states, the correction means corrects at least one of the injection start timing, the injection amount, and the supply pressure in a direction to eliminate the difference. Accordingly, even when the viscosity and/or performance of the fuel has changed with reference to the standard state, the combustion state can be corrected to the standard state.

That is, even when the viscosity and/or performance of the fuel has changed with reference to the standard state, optimum combustion in correspondence with a vehicle running state can be realized, and the degradation of drivability and exhaust gas performance can be prevented.

In another aspect of the present invention, when there is a time difference between a rising start time of the standard state obtained by the standard state estimation means and rising start time of the cylinder internal pressure or the heat release rate detected by the cylinder internal pressure sensor, the correction means corrects the injection start timing in a direction to eliminate the time difference.

In this arrangement, even when the viscosity and/or performance of the fuel has changed with reference to the standard state, the rising start time of cylinder internal pressure or the heat release rate can be corrected to the standard state.

Further, when there is a peak difference between a peak value of the standard state obtained by the standard state estimation means and a peak value of the cylinder internal pressure or the heat release rate detected by the cylinder internal pressure sensor, the correction means corrects the injection amount in a direction to eliminate the peak difference.

In this arrangement, even when the viscosity and/or performance of the fuel has changed with reference to the standard state, the peak value of cylinder internal pressure or the heat release rate can be corrected to the standard state.

Further, when there is a slope angle difference between a rising slope angle of the standard state obtained by the standard state estimation means and a rising slope angle of the cylinder internal pressure or the heat release rate detected by the cylinder internal pressure sensor, the correction means corrects the supply pressure in a direction to eliminate the slope angle difference.

In this arrangement, even if the viscosity and/or performance of the fuel has changed with reference to the standard state, the rising slope angle of cylinder internal pressure or the heat release rate can be corrected to the standard state.

In a fuel injection system according to yet another aspect of the present invention, the injection amount is corrected in correspondence with a viscosity difference between the fuel viscosity detected by the viscosity detection means and a standard viscosity.

In this arrangement, the standard viscosity is compared with the detected fuel viscosity, and when there is a difference between them, the injection amount is corrected in correspondence with the difference. Accordingly, even when the fuel viscosity has been changed with respect to the standard state, an optimum injection amount in correspondence with the vehicle running state can be realized, and the degradation of drivability and exhaust gas performance caused by the change in fuel viscosity with respect to the standard state can be prevented.

In a fuel injection system according to yet another aspect of the present invention, the fuel viscosity is obtained by correcting the fuel viscosity obtained by the pressure loss sensor based on the fuel temperature. Accordingly, the fuel viscosity can be detected with high accuracy, and the accuracy of correction of the injection amount with respect to the fuel viscosity can be improved.

In a fuel injection system according to still another aspect of the present invention, when there is a difference between the standard state of the cylinder internal pressure or the heat release rate obtained by the standard state estimation means and the cylinder internal pressure or the heat release rate detected by the cylinder internal pressure sensor after the execution of the injection amount correction by the viscosity correction means, a cetane value correction means estimates a change value of a cetane value of the fuel based on the difference, and the viscosity correction means further corrects the injection amount based on the cetane value change value.

In this arrangement, because the cetane value (fuel performance) correction in addition to the fuel viscosity correction can be performed, the degradation of drivability and the degradation of exhaust gas performance caused by a change in fuel viscosity with respect to the standard state can be prevented.

Other features and advantages of the present invention will be appreciated, as well as methods of operation and the function of the related parts from a study of the following detailed description, appended claims, and drawings, all of which form a part of this application. In the drawings:

DETAILED DESCRIPTION OF THE PREFERRED EMBODIMENTS

One best mode of the present invention includes an injector that injects fuel to an internal combustion engine; a controller that controls injection start timing to start fuel injection from the injector, an injection amount of injection from the injector, and supply pressure of the fuel supplied to the injector; and a cylinder internal pressure sensor that detects a cylinder internal pressure or a heat release rate of the internal combustion engine.

The controller includes a standard state estimation means for obtaining a standard state of the cylinder internal pressure or the heat release rate upon fuel injection from the injector; and a correction means for, when there is a difference between the standard state obtained by the standard state estimation means and the cylinder internal pressure or the heat release rate detected by the cylinder internal pressure sensor, correcting one or plural of the injection start timing, the injection amount, and the supply pressure in a direction to eliminate the difference.

Another best mode of the present invention includes an injector that injects fuel to an internal combustion engine; a controller that controls an injection amount of injection from the injector; and a viscosity detection means for detecting a fuel viscosity of fuel supplied to the injector.

The controller has a viscosity correction means for correcting the injection amount in correspondence with a viscosity difference between the fuel viscosity detected by the viscosity detection means and a standard viscosity.

Figure 1:
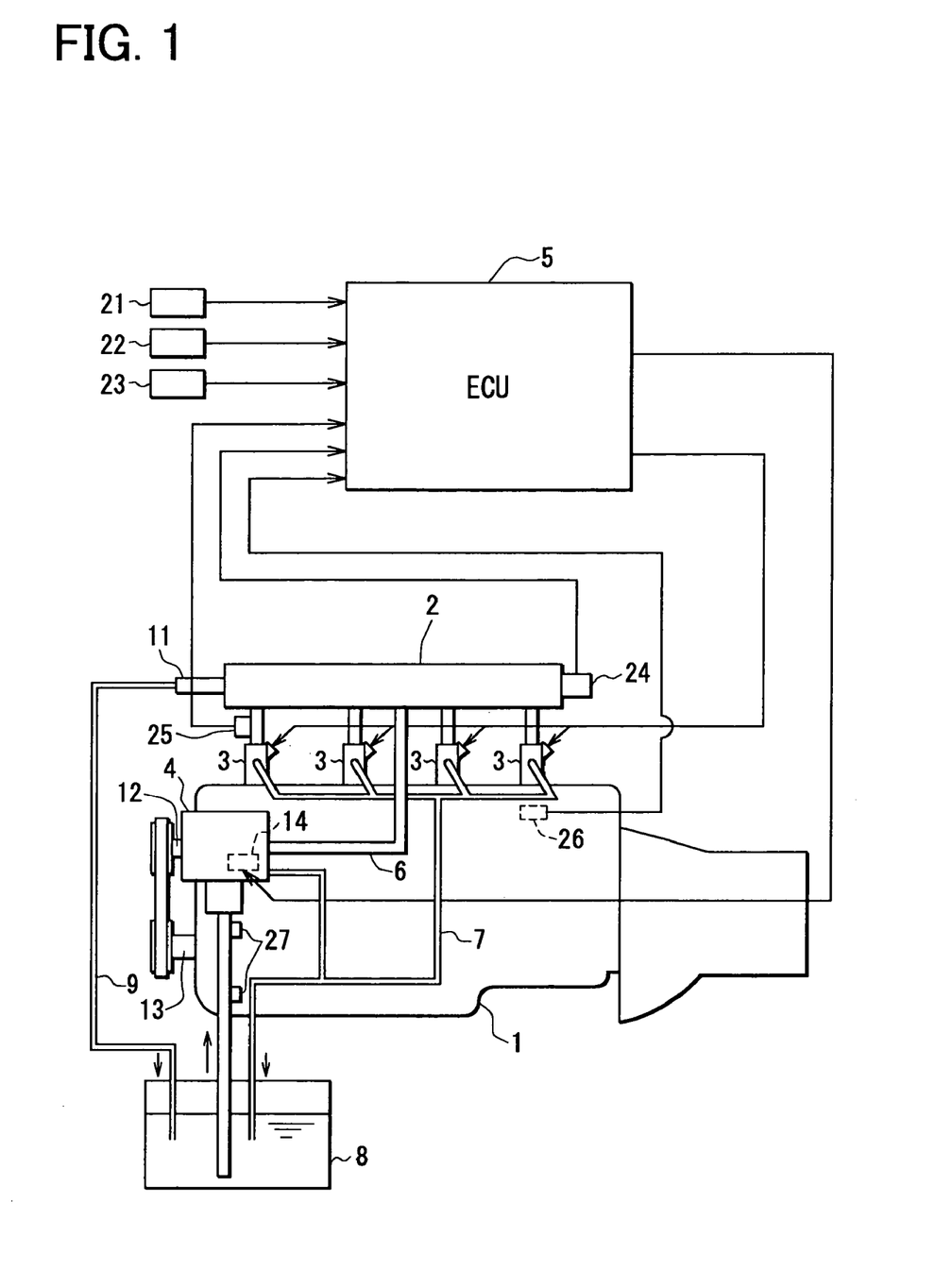
FIG. 1 is a block diagram of a common rail fuel injection system according to the present invention adapted to an internal combustion engine.
Figure 2:
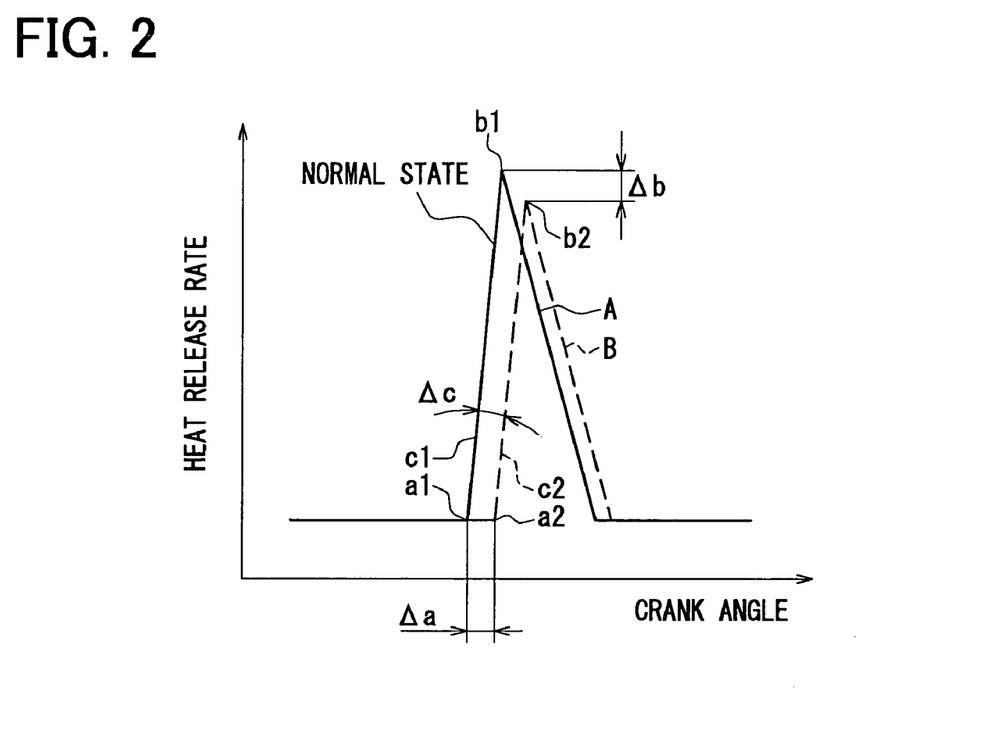
FIG. 2 is a graph showing a change in a heat release rate relative to a crank angle according to a first embodiment of the present invention.

A embodiment where the present invention is applied to a common rail fuel injection system will be described with reference to FIGS. 1 to 3. First, the construction of the common rail fuel injection system will be described with reference to FIG. 1.

The common rail fuel injection system is a system to perform fuel injection on, e.g., a diesel engine (hereinbelow, "engine") 1. The system has a common rail 2, an injector 3, a supply pump 4, an ECU 5 (abbreviation of electric control unit: corresponding to a controller) and the like.

The engine 1 has plural cylinders to continuously perform respective intake, compression, explosion, and exhaust steps. In this embodiment, a 4-cylinder engine is shown, however, any other engine having different number of cylinders may be used.

The common rail 2, which is a pressure-accumulation container for pressure-accumulation of high pressure fuel to be supplied to the injector 3, is connected to a discharge orifice of the supply pump 4 which transfers the high pressure fuel via a fuel pipe (high pressure fuel channel) 6, so as to accumulate a common rail pressure corresponding to a fuel injection pressure.

Note that leak fuel from the injector 3 is returned to a fuel tank 8 through a leak pipe (fuel backflow channel) 7.

Further, a pressure limiter 11 is attached to a relief pipe (fuel backflow channel) 9 from the common rail 2 to a fuel tank 8. The pressure limiter 11, which is a pressure safety valve, is opened when the fuel pressure in the common rail 2 has exceeded a limit pressure, so as to suppress the fuel pressure in the common rail 2 to or lower than the limit pressure.

The injector 3, which is mounted in the respective cylinders of the engine 1, inject-supplies the fuel to the respective cylinders. The injector has a fuel injection nozzle, connected to a downstream side end of plural branch pipes branched from the common rail 2, to inject-supply the high pressure fuel pressure-accumulated in the common rail 2 to the respective cylinders, and an electromagnetic valve to lift-control a needle accommodated in the fuel injection nozzle.

The electromagnetic valve of the injector 3 controls injection start timing and injection amount by an injector opening valve signal supplied from the ECU 5. The high pressure fuel is inject-supplied to the cylinders by the injector opening valve signal supplied to the electromagnetic valve, and the fuel injection is stopped when the injector opening valve signal is OFF.

The supply pump 4, which is a fuel pump to transfer the high pressure fuel to the common rail 2, has a feed pump to suck the fuel in the fuel tank 8 to the supply pump 4, and a high pressure pump to compress the fuel sucked by the feed pump to high pressure and transfer the fuel to the common rail 2. The feed pump and the high pressure pump are driven by a common cam shaft 12. Note that as shown in FIG. 1, the cam shaft 12 is rotatably driven by a crankshaft 13 or the like of the engine 1.

Further, a pump control valve (hereinbelow, SCV) 14 to control the amount of fuel to be sucked to the high pressure pump is mounted in the supply pump 4. The common rail pressure (supply pressure of fuel to the injector 3) is controlled by controlling the SCV 14 by the ECU 5.

The ECU 5 comprises a microcomputer having a well-known construction including a CPU for control processing and computation processing, a storage device (a memory such as ROM, stand-by RAM, EEPROM, or a RAM) for storing various programs and data, an input circuit, an output circuit, and a power source circuit. Note that in this embodiment, an EDU (abbreviation of electric drive unit: an injector driving circuit and a pump driving circuit) integrated with the ECU 5 is mounted, however, the EDU may be mounted separately from the ECU.

The ECU 5 performs various computation processings based on read signals from sensors (engine parameters: signals corresponding to a driver's running state, a running state of the engine 1 and the like).

Note that an accelerator sensor 21 to detect an accelerator opening, a revolution sensor 22 to detect the number of engine revolutions, a water temperature sensor 23 to detect the temperature of cooling water for the engine 1, a common rail pressure sensor 24 to detect the common rail pressure, a fuel temperature sensor 25 to detect a fuel temperature, and the like, are connected as sensors to detect the engine parameters to the ECU 5.

Upon each fuel injection, the ECU 5 performs driving control (injection control) on the injector 3 and driving control (opening control) on the SCV 14 in the supply pump 4 based on the programs (maps and the like) stored in the ROM and the engine parameters read into the RAM.

The ECU 5 has an injection timing calculation function and an injection period calculation function as driving control programs for the injector 3.

The ECU 5 has an SCV opening calculation function as a control program for the SCV 14.

The injection timing calculation function is a control program to obtain target injection start timing T corresponding to a current running state, obtain a command injection timing to start injection at the injection start timing T, and to generate an injection start signal (more particularly, start of ON state of the injection signal) in the injector driving circuit of the EDU at the command injection timing.

The injection period calculation function is a control program to obtain a target injection amount Q corresponding to a current running state, to obtain a command injection period to obtain the injection amount Q, and to generate an injection continuous signal (more particularly, the continuation of ON state of the injection signal) to perform injection during the command injection period.

The SCV opening calculation function is a control program to obtain a target common rail pressure P (corresponding to the supply pressure) corresponding to a current running state, to calculate an SCV opening when an real common rail pressure detected by the common rail pressure sensor 24 is the common rail pressure P, and to generate a valve opening signal (for example, a PWM signal) by the pump driving circuit of the EDU so as to obtain the calculated SCV opening in the SCV 14.

As described above, the ECU 5 calculates optimum injection start timing T, injection amount Q, and common rail pressure P from a current vehicle running state (the engine parameters detected by the sensors), then starts fuel injection from the injector 3 at the injection start timing T obtained by computation at the common rail pressure P obtained by computation, and performs injection from the injector 3 by the injection amount Q obtained by computation.

However, even if the precision of the parts such as the injector 3 is increased to the maximum, when the viscosity, the cetane value and the like of the fuel supplied to the injector 3 have changed, the heat release rate in the cylinder changes as an real heat release rate (hereinbelow, referred to as an "real heat release rate") B in FIG. 2 with respect to a target heat release rate (standard state) A in FIG. 2.

More particularly, when the viscosity, the cetane value and the like of the fuel have changed, (1) a rising start time a2 of the real heat release rate B may change with respect to a rising start time a1 of the target heat release rate A, (2) a peak value b2 of the real heat release rate B may change with respect to a peak value b1 of the target heat release rate A, or (3) a rising slope angle c2 of the real heat release rate B may change with respect to a rising slope angle c1 of the target heat release rate A.

Figure 3:
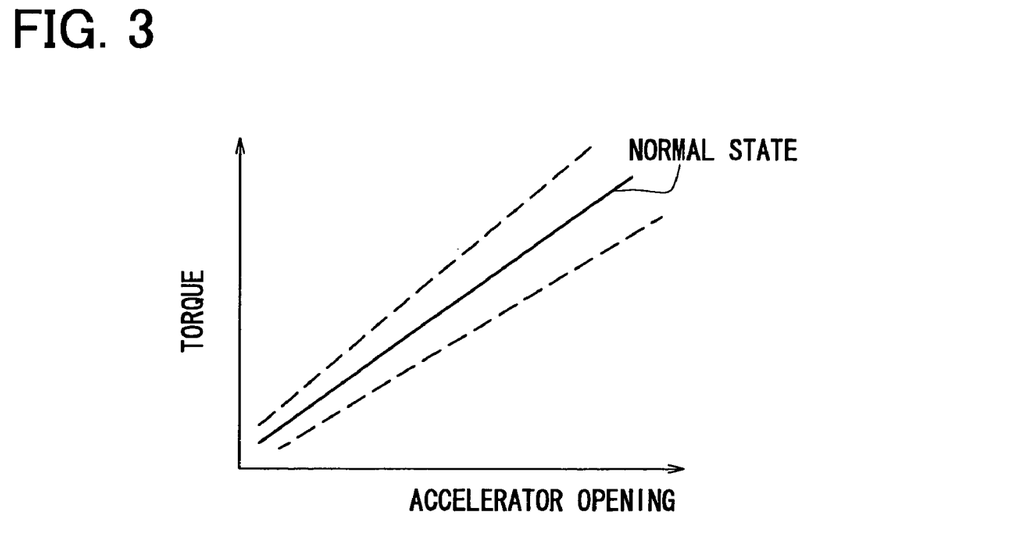
FIG. 3 is a graph showing a relationship between an accelerator opening and engine torque according to the first embodiment of the present invention.

In this manner, when the viscosity, the cetane value and the like of the fuel have changed, as shown in FIG. 3, an engine torque to be obtained in correspondence with accelerator opening changes, which degrades the drivability performance. Further, the air-fuel ratio changes with respect to a target value, which degrades the exhaust gas performance. Note that the solid line in FIG. 3 shows a characteristic diagram between the accelerator opening and the torque in the standard state (standard fuel), and the broken lines in FIG. 3 is a characteristic diagram between the accelerator opening and the torque in the case of fuel having viscosity and cetane value different from the standard state (standard fuel).

Accordingly, the function of correction means for comparing the target heat release rate A with the real heat release rate B, and correcting the injector 3 and the SCV 14 based on the difference so as to bring the target heat release rate A and the real heat release rate B into correspondence, is programmed in the ECU 5 of this embodiment 1.

The common rail fuel injection system has a cylinder internal pressure sensor 26 to detect a cylinder internal pressure of the engine 1. The cylinder internal pressure sensor 26 of this embodiment 1 has an approximate growplug shape. A sensor portion arranged at its end, inserted into each combustion chamber of the engine 1, directly detects each cylinder internal pressure. Note that the cylinder internal pressure sensor 26 may be provided in all the cylinders or in any one of the cylinder.

The ECU 5 is provided with standard state estimation means (program) for obtaining the target heat release rate A (standard state) upon fuel injection, and real state estimation means (program) for estimating the real heat release rate B from the cylinder internal pressure detected by the cylinder internal sensor 26.

Further, the ECU 5 is provided with correction means (program) for, when there is a difference between the target heat release rate A obtained by the standard state estimation means and the real heat release rate B obtained by the real state estimation means, correcting one or plural of the injection start timing, the injection amount, and the common rail pressure in a direction to eliminate the difference.

The correction means of this embodiment 1 comprises (1) timing correction means (program) (2) injection amount correction means (program) and (3) rail pressure correction means (program), for comparing the target heat release rate A obtained by the standard state estimation means with the real heat release rate B obtained by the real state estimation means, and correcting the injection start timing T, correcting the injection amount Q, and correcting the common rail pressure P.

The timing correction means is a program to, when there is a time difference ($\Delta a \neq 0$) between the rising start time a1 of the target heat release rate A obtained by the standard state estimation means and the rising start time a2 of the real heat release rate B obtained by the real state estimation means ($\Delta a = a1 - a2$), correct the injection start timing T in a direction to eliminate the time difference $\Delta a$.

More particularly, when the rising start time a2 is delayed from the rising start time a1 ($0 < \Delta a = a1 - a2$), correction to precipitate the injection start timing T is performed as the difference increases. On the other hand, when the rising start time a2 is ahead of the rising start time a1 ($0 > \Delta a = a1 - a2$), correction to delay the injection start timing T is performed as the difference increases. The computation is obtained from a map or expression.

The injection amount correction means is a program to, when there is a peak difference ($\Delta b \neq 0$) between the peak value b1 of the target heat release rate A obtained by the standard state estimation means and the peak value b2 of the real heat release rate B obtained by the real state estimation means ($\Delta b = b1 - b2$), correct the injection amount Q in a direction to eliminate the peak difference $\Delta b$.

More particularly, when the peak value b2 is less than the peak value b1 ($0 < \Delta b = b1 - b2$), correction to increase the injection amount Q is performed as the difference increases. On the other hand, when the peak value b2 is greater than the peak value b1 ($0 > \Delta b = b1 - b2$), correction to reduce the injection amount Q is performed as the difference increases. The computation is obtained from a map or expression.

The rail pressure correction means is a program to, when there is a slope angle difference ($\Delta c \neq 0$) between the rising slope angle c1 of the target heat release rate A obtained by the standard state estimation means and the rising slope angle c2 of the real heat release rate B obtained by the real state estimation means ($\Delta c = c1 - c2$), correct the common rail pressure P in a direction to eliminate the slope angle difference $\Delta c$.

More particularly, when the rising slope angle c2 is smaller than the rising slope angle c1 ($0 < \Delta c = c1 - c2$), correction to increase the common rail P is performed as the difference increases. On the other hand, when the rising slope angle c2 is larger than the rising slope angle c1 ($0 > \Delta c = c1 - c2$), correction to reduce the common rail P is performed as the difference increases. The computation is obtained from a map or expression.

As described above, in the common rail fuel injection system of this embodiment, the target heat release rate A obtained by the standard state estimation means is compared with the real heat release rate B obtained by the real state estimation means, and when there is a difference between the both rates, the correction means corrects one or plural of the injection start timing T, the injection amount Q, and the common rail pressure P in a direction to eliminate the difference. In this arrangement, even when the viscosity and/or the cetane value of the fuel has changed with respect to the standard, the combustion state in each cylinder can be corrected to the target heat release rate A.

More particularly, when there is a time difference $\Delta a$ ($\Delta a \neq 0$) between the rising start time a1 of the target heat release rate A and the rising start time a2 of the real heat release rate B obtained by the real state estimation means, the timing correction means corrects the injection start timing T in a direction to eliminate the time difference $\Delta a$. Accordingly, even when the viscosity and/or the cetane value of the fuel has changed, the rising start time a2 of the real heat release rate B can be corrected to the standard (the rising start time a1).

Further, when there is a peak difference $\Delta b$ ($\Delta b \neq 0$) between the peak value b1 of the target heat release rate A and the peak value b2 of the real heat release rate B obtained by the real state estimation means, the injection amount correction means corrects the injection amount Q in a direction to eliminate the time difference $\Delta b$. Accordingly, even when the viscosity and/or the cetane value of the fuel has changed, the peak value b2 of the real heat release rate B can be corrected to the standard (the peak value b1).

Further, when there is a slope angle difference $\Delta c$ ($\Delta c \neq 0$) between the rising slope angle c1 of the target heat release rate A and the rising slope angle c2 of the real heat release rate B obtained by the real state estimation means, the rail pressure correction means corrects the common rail pressure P in a direction to eliminate the time difference $\Delta c$. Accordingly, even when the viscosity and/or the cetane value of the fuel has changed, the rising slope angle c2 of the real heat release rate B can be corrected to the standard (the rising slope angle c1).

In this manner, in the common rail fuel injection system of the embodiment 1, even when the viscosity and/of the cetane value of the fuel has changed with respect to the standard, optimum combustion corresponding to a vehicle running state can be realized. Thus, the degradation of drivability performance and the degradation of exhaust gas performance caused by change of viscosity and/or cetane value of the fuel with respect to the standard can be prevented. That is, even when the viscosity and/or the cetane value of fuel has changed with respect to the standard, high-accuracy air-fuel ratio control can be performed. Accordingly, the fuel consumption can be improved to the maximum, and the exhaust gas performance can be improved to the maximum.

A second embodiment will be described with reference to FIG. 4. Note that in the following embodiment, the same reference numerals as those in the above embodiment 1 indicate the same functional elements.

When the fuel viscosity has become higher than the standard, as the fuel does not easily flow, the real injection amount Q' of injection from the injector 3 becomes lower than the target injection amount Q.

On the other hand, when the fuel viscosity has become lower than the standard, as the fuel easily flows, the real injection amount Q' of injection from the injector 3 becomes higher than the target injection amount Q the viscosity increases.

Accordingly, in the common rail fuel injection system of the second embodiment, the injection amount is corrected in correspondence with change in fuel viscosity. The system has viscosity detection means for detecting a fuel viscosity N of fuel supplied to the injector 3, and viscosity correction means (program) for correcting the injection amount Q based on the fuel viscosity N detected by the viscosity detection means.

When the fuel viscosity N detected by the viscosity detection means is higher than a standard viscosity $N_0$ ($N > N_0$), the viscosity correction means performs correction to increase the injection amount Q (more particularly, correction to increase a valve opening period in the injector 3) as the difference ($N - N_0$) from the standard viscosity increases. The computation is obtained from a map or expression.

In this arrangement, as the fuel viscosity N increases and the fuel does not flow easily, the correction to increase the injection amount Q is performed. Thus, the real injection amount Q' of injection from the injector 3 is brought into correspondence with the target injection amount Q.

Figure 4:
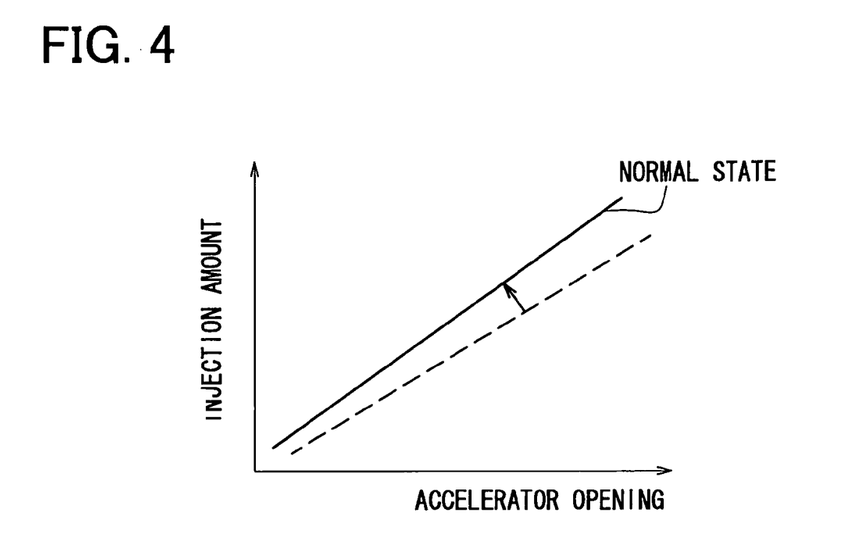
FIG. 4 is a graph showing a relationship between the accelerator opening and an injection amount according to a second embodiment of the present invention.

More particularly, as indicated with a broken line in FIG. 4, when the fuel viscosity N has become higher than the standard viscosity $N_0$, as the fuel does not easily flow, the injection amount becomes less than the target injection amount Q (standard state) with respect to the accelerator opening without correction. However, as the correction is performed so as to increase the injection amount Q as the fuel viscosity N becomes higher than the standard viscosity N0, the real injection amount Q' of injection from the injector 3 is brought into correspondence with the target injection amount Q as indicated with a solid line in FIG. 4.

Further, when the fuel viscosity N detected by the viscosity detection means is lower than the standard viscosity $N_0$ ($N<N_0$), the viscosity correction means performs correction to reduce the injection amount Q (more particularly, correction to reduce the valve opening period in the injector 3) as the difference from the standard viscosity $N_0$ increases. The computation is obtained from a map or expression.

In this arrangement, as the fuel viscosity N becomes lower than the standard viscosity $N_0$ and the fuel flows easily, the correction to reduce the injection amount Q is performed. Thus the real injection amount Q' of injection from the injector 3 is brought into correspondence with the target injection amount Q.

The viscosity detection means of this embodiment has a pressure loss sensor to detect a pressure loss in a fuel pipe to supply the fuel to the injector 3 and a fuel temperature sensor 25 to detect a fuel temperature supplied to the injector 3. The ECU 5 obtains the fuel viscosity N by correcting the fuel viscosity, obtained based on the pressure loss detected by the pressure loss sensor, with the fuel temperature detected by the fuel temperature sensor 25. In this manner, in this embodiment, as the fuel viscosity N is obtained by correcting the fuel viscosity obtained by the pressure loss sensor with the fuel temperature, the fuel viscosity N can be detected with high accuracy, and the accuracy of correction to the injection amount Q with respect to the fuel viscosity N can be increased.

Note that as an example of the pressure loss sensor, detection means using pressure sensors in two positions, or detection means using a flow meter is known.

The detection means using pressure sensors in two positions will be described with reference to FIG. 1. A pressure sensor 27 to detect a fuel pressure is provided on the upstream side and the downstream side of a pipe where the fuel flows (for example, a pipe to supply the fuel from the fuel tank 8 to the supply pump 4). The pressure loss of the fuel supplied to the injector 3 is detected from a pressure difference between the two pressure sensor values 27.

Further, the detection means using a flow meter measures a flow amount of the fuel in the pipe where the fuel flows (for example, a pipe to supply the fuel from the fuel tank 8 to the supply pump 4), and detects the pressure loss of the fuel supplied to the injector 3 from a flow amount (easiness of flowing) of the fuel.

In the common rail fuel injection system of the embodiment 2, the standard viscosity $N_0$ is compared with the fuel viscosity N of fuel supplied to the injector 3, and when there is a difference between the viscosities, the injection amount Q is corrected in accordance with the difference. Even when the fuel viscosity N has changed with respect to the standard viscosity $N_0$, an optimum injection amount corresponding to a vehicle running state can be realized. Accordingly, the degradation of drivability performance and the degradation of exhaust gas performance caused by the change of the fuel viscosity N with respect to the standard viscosity $N_0$ can be prevented.

Note that in the embodiment 2, when the fuel viscosity N detected by the viscosity detection means is higher than the standard viscosity $N_0$ ($N>N_0$), the correction to increase the injection amount Q is performed as the difference ($N-N_0$) increases, on the other hand, when the fuel viscosity N detected by the viscosity detection means is lower than the standard viscosity N0 ($N<N_0$), the correction to reduce the injection amount Q is performed as the difference ($N_0-N$) increases.

However, there is a probability that the increase in the injection period by pressure change in the control chamber (nozzle back pressure chamber) is greater than the amount of reduction of the real injection amount Q' of injection from the injector 3 by the increase in the fuel viscosity. In such case, the injection amount Q is corrected in opposite directions to those in the control shown in the present embodiment 2. That is, when the fuel viscosity N detected by the viscosity detection means is higher than the standard viscosity $N_0$ ($N>N_0$), the correction to reduce the injection amount Q is performed as the difference ($N-N_0$) increases, on the other hand, when the fuel viscosity N detected by the viscosity detection means is lower than the standard viscosity $N_0$ ($N<N_0$), the correction to increase the injection amount Q as the difference ($N_0-N$) increases.

A third embodiment will be described with reference to FIG. 5.

In the above embodiment 2, the injection amount Q is corrected in accordance with only the fuel viscosity. However, there is a probability that only the correction to the injection amount Q based on the fuel viscosity N can not prevent the change of the heat release rate in the cylinder when the cetane value of the fuel has changed, which may cause degradation of drivability performance.

Accordingly, in the common rail fuel injection system of the embodiment 3, the injection amount is corrected in correspondence with the change in cetane value, in addition to the viscosity correction means (the correction function for the injection amount Q based on fuel viscosity). The system has cetane-value change estimation means for estimating a cetane value change amount (cetane value change value) S with respect to the standard fuel, and cetane value correction means for correcting the injection amount Q based on the cetane value change value S detected by the cetane-value change value estimation means.

The cetane-value change estimation means estimates the cetane value change value S with respect to the standard fuel using the cylinder internal pressure sensor 26 shown in the embodiment 1.

As in the case of the embodiment 1, the ECU 5 has standard state estimation means for obtaining the target heat release rate A (see a solid line in FIG. 5) upon fuel injection and real state estimation means for estimating a real heat release rate B (see a broken line in FIG. 5) from the cylinder internal pressure detected by the cylinder internal pressure sensor 26.

The target heat release rate A obtained by the standard state estimation means is compared with the real heat release rate B obtained by the real state estimation means, and the cetane value change value S is estimated from the difference between these rates.

As examples of means for estimating the cetane value change value S from the difference between the target heat release rate A and the real heat release rate B, peak value comparison means and rising slope angle comparison means will be described.

Figure 5:
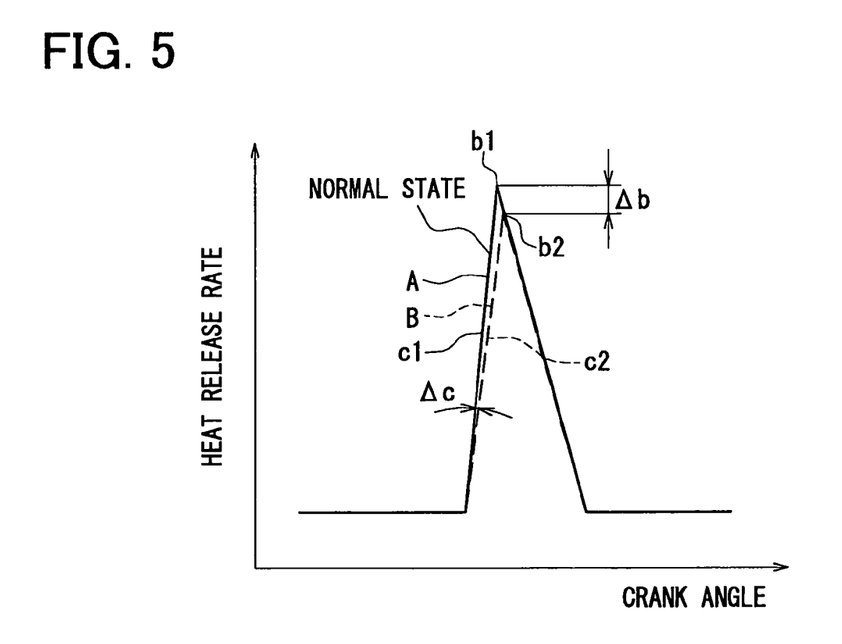
FIG. 5 is a graph showing a change in a heat release rate relative to a crank angle according to a third embodiment of the present invention.

As shown in FIG. 5, the peak value comparison means estimates the cetane value change value S by a map or expression from a peak difference ($\Delta b=b1-b2$) between a peak value b1 of the target heat release rate A obtained by the standard state estimation means and a peak value b2 of the real heat release rate B obtained by the real state estimation means.

As shown in FIG. 5, the rising slope angle comparison means estimates the cetane value change value S by a map or expression from a slope angle difference ($\Delta c=c1-c2$) between a rising slope angle c1 of the target heat release rate A obtained by the standard state estimation means and a rising slope angle c2 of the real heat release rate B obtained by the real state estimation means.

When the correction to the injection amount has been performed by the viscosity correction means (see the embodiment 2), the cetane value correction means estimates the cetane value change value S by the cetane-value change value estimation means, and corrects the injection amount Q based on the estimated cetane value change value S.

More particularly, when the cetane value is greater than the standard fuel, the cetane value correction means performs correction to reduce the injection amount Q (more particularly, correction to reduce the valve opening period in the injector 3) as the cetane value change value S increases to the +side. The computation is obtained from a map or expression. In this arrangement, as the correction to reduce the injection amount Q is performed as the cetane value becomes greater than the standard fuel, the real heat release rate B obtained by the real state estimation means can be approximated to the target heat release rate A obtained by the standard state estimation means.

On the other hand, when the cetane value is less than the standard fuel, the cetane value correction means performs correction to increase the injection amount Q (more particularly, correction to increase the valve opening period in the injector 3) as the cetane value change value S increases to the −side. The computation is obtained from a map or expression.

In this arrangement, as the correction to increase the injection amount Q is performed as the cetane value becomes less than the standard fuel, the real heat release rate B obtained by the real state estimation means can be approximated to the target heat release rate A obtained by the standard state estimation means.

In the common rail fuel injection system of the embodiment 3, in addition to the correction to the fuel viscosity, the cetane value is corrected. Accordingly, combustion in correspondence with fuel characteristic (viscosity and cetane value) can be realized. In this arrangement, even when the fuel viscosity and/or the cetane value has changed, the degradation of drivability performance and the degradation of exhaust gas performance can be suppressed with high accuracy.

In the above embodiment, as the cylinder internal pressure sensor 26, a sensor is inserted into the cylinder of the engine 1 so as to directly detect the cylinder internal pressure, however, it may be arranged such that an acceleration sensor or the like is attached to the engine 1 and the cylinder internal pressure is calculated from vibration of the engine 1 or the like detected by the acceleration sensor. Further, any other means e.g. use of a ring cylinder internal pressure sensor (pressure sensor) in a gasket of the injector 3, a glow plug, or a spark plug (gasoline engine or the like), may be employed.

In the above embodiment, the heat release rate is calculated from the cylinder internal pressure, and the target heat release rate A is compared with the real heat release rate B. However, it may be arranged such that the cylinder internal pressure detected by the cylinder internal pressure sensor is compared with a target cylinder internal pressure.

In the above embodiment, the present invention is applied to a common rail fuel injection system where leak fuel occurs upon actuation of the injector 3, however, the present invention may be applied to a common rail fuel injection system where a linear solenoid mounted in the injector 3 directly drives the needle and leak fuel does not occur. That is, the present invention may be applied to a fuel injection system having an injector where the needle is directly driven such as a piezo injector or the like.

In the above embodiment, the present invention is applied to a common rail fuel injection system, however, the present invention may be applied to a fuel injection system without common rail. That is, the present invention may be applied to a fuel injection system used in other engines than the diesel engine such as a gasoline engine for correction to injection amount. Note that in a case where the present invention is applied to a gasoline engine, the cetane value in the working embodiment is replaced with an octane value.

What is claimed is:

1. A fuel injection system comprising:
    an injector that injects fuel to an internal combustion engine;
    a controller that controls an injection start timing to start fuel injection from the injector, an injection amount of injection from the injector, and a supply pressure of the fuel supplied to the injector; and
    a cylinder internal pressure sensor that detects one of a cylinder internal pressure and a heat release rate of the internal combustion engine,
    wherein the controller includes:
    standard state estimation means for obtaining a standard state of one of the cylinder internal pressure and the heat release rate upon fuel injection from the injector; and
    correction means for correcting at least one of the injection start timing, the injection amount, and the supply pressure in a direction to eliminate a difference that exists between the standard state obtained by the standard state estimation means and one of the cylinder internal pressure and the heat release rate detected by the cylinder internal pressure sensor.

2. The fuel injection system according to claim 1, wherein
    the correction means corrects the injection start timing in a direction to eliminate a time difference when the time difference exists between a rising start time of the standard state obtained by the standard state estimation means and a rising start time of one of the cylinder internal pressure and the heat release rate detected by the cylinder internal pressure sensor,
    the correction means corrects the injection amount in a direction to eliminate a peak difference when the peak difference exists between a peak value of the standard state obtained by the standard state estimation means and a peak value of one of the cylinder internal pressure and the heat release rate detected by the cylinder internal pressure sensor, and
    the correction means corrects the supply pressure in a direction to eliminate a slope angle difference when the slope angle difference exists between a rising slope angle of the standard state obtained by the standard state estimation means and a rising slope angle of one of the cylinder internal pressure and the heat release rate detected by the cylinder internal pressure sensor.

3. The fuel injection system as in claim 1, wherein the internal combustion engine is a diesel engine.

4. A fuel injection system comprising:
    an injector that injects fuel to an internal combustion engine;
    a controller that controls an injection amount of injection from the injector; and
    viscosity detection means for detecting a fuel viscosity of fuel supplied to the injector, the detection means including a pressure loss sensor that detects a pressure loss in a fuel pipe supoplying the fuel to the injector, the viscosity detector means detecting the fuel viscosity based on the pressure loss detected by the pressure loss sensor, wherein the controller has viscosity correction means for correcting the injection amount in correspondence with a viscosity difference between the fuel viscosity detected by the viscosity detection means and a standard viscosity.

5. The fuel injection system according to claim 4, further comprising:

a fuel temperature sensor that detects a fuel temperature supplied to the injector, wherein the standard viscosity is obtained by correcting the fuel viscosity obtained based on the pressure loss detected by the pressure loss sensor with the fuel temperature detected by the fuel temperature sensor.

6. The fuel injection system according to claim 5, wherein the fuel injection system comprises a cylinder internal pressure sensor that detects one of a cylinder internal pressure and a heat release rate of the internal combustion engine, wherein the control means has:

standard state estimation means for obtaining a standard state of one of the cylinder internal pressure and the heat release rate upon fuel injection from the injector; and cetane value correction means for estimating a change value of a cetane value of the fuel from a difference that exists between the standard state obtained by the standard state estimation means and one of the cylinder internal pressure and the heat release rate detected by the cylinder internal pressure sensor after the execution of injection amount correction by the viscosity correction means, and further correcting the injection amount corrected by the viscosity correction means based on the change value of the cetane value.

7. The fuel injection system according to claim 4, wherein the fuel injection system comprises a cylinder internal pressure sensor that detects one of a cylinder internal pressure and a heat release rate of the internal combustion engine, wherein the control means has:

standard state estimation means for obtaining a standard state of one of the cylinder internal pressure and the heat release rate upon fuel injection from the injector; and cetane value correction means for estimating a change value of a cetane value of the fuel from a difference that exists between the standard state obtained by the standard state estimation means and one of the cylinder internal pressure and the heat release rate detected by the cylinder internal pressure sensor after the execution of injection amount correction by the viscosity correction means, and further correcting the injection amount corrected by the viscosity correction means based on the change value of the cetane value.

8. The fuel injection system as in claim 4, wherein the internal combustion engine is a diesel engine.

9. A fuel injection system comprising:

an injector that injects fuel to an internal combustion engine;

a controller that controls an injection amount of injection from the injector;

a viscosity detector having a pressure loss sensor that detects a pressure loss in a fuel pipe supplying the fuel to the injector, the viscosity detector detecting a fuel viscosity of fuel supplied to the injector based on the pressure loss detected by the pressure loss sensor; and a fuel temperature sensor that detects a fuel temperature supplied to the injector, wherein the controller has viscosity correction means for correcting the injection amount in correspondence with a viscosity difference between the fuel viscosity detected by the viscosity detection means and a standard viscosity, and the standard viscosity is obtained by correcting the fuel viscosity obtained based on the pressure loss detected by the pressure loss sensor with the fuel temperature detected by the fuel temperature sensor.

10. The fuel injection system according to claim 9, wherein the fuel injection system comprises a cylinder internal pressure sensor that detects one of a cylinder internal pressure and a heat release rate of the internal combustion engine, wherein the control means has:

standard state estimation means for obtaining a standard state of one of the cylinder internal pressure and the heat release rate upon fuel injection from the injector; and cetane value correction means for estimating a change value of a cetane value of the fuel from a difference that exists between the standard state obtained by the standard state estimation means and one of the cylinder internal pressure and the heat release rate detected by the cylinder internal pressure sensor after the execution of injection amount correction by the viscosity correction means, and further correcting the injection amount corrected by the viscosity correction means based on the change value of the cetane value.

11. The fuel injection system as in claim 9, wherein the internal combustion engine is a diesel engine.

* * * * *